(12) United States Patent
Campos

(10) Patent No.: US 8,075,478 B2
(45) Date of Patent: Dec. 13, 2011

(54) SYSTEM, APPARATUS, AND METHOD FOR VIEWING A VISUALLY OBSCURED PORTION OF A CAVITY

(76) Inventor: Jorge A. Campos, Mexico City (MX)

(*) Notice: Subject to any disclaimer, the term of this patent is extended or adjusted under 35 U.S.C. 154(b) by 0 days.

(21) Appl. No.: 10/829,833

(22) Filed: Apr. 22, 2004

(65) Prior Publication Data

US 2004/0249246 A1    Dec. 9, 2004

Related U.S. Application Data

(60) Provisional application No. 60/464,602, filed on Apr. 22, 2003.

(51) Int. Cl.
    *A61B 1/00* (2006.01)
(52) U.S. Cl. ........ 600/139; 600/111; 600/127; 600/129; 600/138; 600/160
(58) Field of Classification Search .............. 600/111, 600/127, 129, 160
    See application file for complete search history.

(56) References Cited

U.S. PATENT DOCUMENTS

| | | | | |
|---|---|---|---|---|
| 4,132,227 A | * | 1/1979 | Ibe | .................. 600/105 |
| 4,557,255 A | | 12/1985 | Goodman | |
| 4,651,201 A | | 3/1987 | Schoolman | |
| 4,690,175 A | * | 9/1987 | Ouchi et al. | .................. 138/131 |
| 4,718,406 A | | 1/1988 | Bregman | |
| 4,748,969 A | | 6/1988 | Wardle | |
| 4,802,461 A | | 2/1989 | Cho | |
| 4,899,733 A | | 2/1990 | DeCastro | |
| 4,977,887 A | * | 12/1990 | Gouda | .................. 600/144 |
| 5,083,549 A | * | 1/1992 | Cho et al. | .................. 600/108 |
| 5,127,393 A | * | 7/1992 | McFarlin et al. | .................. 600/114 |
| 5,199,417 A | | 4/1993 | Muller | |
| D335,710 S | | 5/1993 | Ainger | |
| 5,217,002 A | * | 6/1993 | Katsurada et al. | .................. 600/139 |
| 5,299,562 A | | 4/1994 | Heckele | |
| 5,308,342 A | * | 5/1994 | Sepetka et al. | .................. 604/525 |
| 5,358,493 A | * | 10/1994 | Schweich et al. | .................. 604/264 |

(Continued)

FOREIGN PATENT DOCUMENTS

DE    100 52 679 A1    5/2001

(Continued)

OTHER PUBLICATIONS

Circon ACMI, USA Series catalog of Urology Endoscopy Products (12 pages).

(Continued)

*Primary Examiner* — Matthew J Kasztejna
(74) *Attorney, Agent, or Firm* — Greenberg Traurig LLP; Ben D. Tobor

(57) ABSTRACT

A system, apparatus, and method for viewing a visually obscured portion of a body cavity. The system includes an endoscopic-type instrument, an imaging apparatus, and a human interface apparatus. The endoscopic-type instrument includes a face tip assembly connected to a shaft assembly, the shaft assembly being connected to a handle and viewing assembly. The face tip assembly includes a plurality of input/output ports and a working channel extension to protect an optical image collector. The shaft assembly includes an actively flexible shaft segment and a passively flexible shaft. The method for viewing a visually obscured portion of a cavity includes the steps of providing an instrument having an actively flexible shaft segment and manipulating the actively flexible shaft segment to a desired angular deflection.

62 Claims, 4 Drawing Sheets

U.S. PATENT DOCUMENTS

| | | | | |
|---|---|---|---|---|
| 5,436,655 | A | 7/1995 | Hiyama | |
| 5,448,988 | A * | 9/1995 | Watanabe | 600/139 |
| 5,459,605 | A | 10/1995 | Kempf | |
| 5,482,029 | A * | 1/1996 | Sekiguchi et al. | 600/109 |
| 5,512,034 | A * | 4/1996 | Finn et al. | 600/138 |
| 5,533,985 | A * | 7/1996 | Wang | 604/264 |
| 5,577,991 | A | 11/1996 | Akui | |
| 5,593,405 | A | 1/1997 | Osypka | |
| 5,735,792 | A * | 4/1998 | Vanden Hoek et al. | 600/138 |
| 5,751,341 | A | 5/1998 | Chaleki | |
| 5,785,644 | A | 7/1998 | Grabover et al. | |
| 5,857,962 | A | 1/1999 | Bracci et al. | |
| 5,857,964 | A | 1/1999 | Konstorum et al. | |
| 5,876,330 | A | 3/1999 | Grabover | |
| 5,885,208 | A * | 3/1999 | Moriyama | 600/144 |
| 5,924,976 | A * | 7/1999 | Stelzer et al. | 600/106 |
| 5,938,588 | A | 8/1999 | Grabover | |
| 5,944,655 | A | 8/1999 | Becker | |
| 6,165,123 | A | 12/2000 | Thompson | |
| 6,171,235 | B1 | 1/2001 | Konstorum et al. | |
| 6,174,280 | B1 * | 1/2001 | Oneda et al. | 600/121 |
| 6,197,015 | B1 * | 3/2001 | Wilson | 604/524 |
| 6,217,511 | B1 | 4/2001 | Held | |
| 6,248,060 | B1 | 6/2001 | Buess | |
| 6,458,076 | B1 * | 10/2002 | Pruitt | 600/146 |
| 6,475,140 | B1 | 11/2002 | Konstorum | |
| 6,485,411 | B1 * | 11/2002 | Konstorum et al. | 600/139 |
| 6,498,884 | B1 | 12/2002 | Colvin | |
| 6,503,194 | B2 | 1/2003 | Pauker | |
| 6,524,299 | B1 * | 2/2003 | Tran et al. | 604/523 |
| 6,749,560 | B1 | 6/2004 | Konstorum et al. | |
| 6,780,151 | B2 | 8/2004 | Grabover et al. | |
| 6,860,849 | B2 * | 3/2005 | Matsushita et al. | 600/140 |
| 2002/0082474 | A1 | 6/2002 | Yamamoto | |
| 2002/0191074 | A1 | 12/2002 | Ogawa | |
| 2003/0023142 | A1 | 1/2003 | Grabover et al. | |

FOREIGN PATENT DOCUMENTS

| | | |
|---|---|---|
| JP | 01-307719 | 12/1989 |
| JP | 2001-161631 | 6/2001 |
| JP | 200309332 | 2/2003 |
| JP | 2003-093325 | 4/2003 |
| WO | WO 02/24058 A2 | 3/2002 |

OTHER PUBLICATIONS

Karl Storz catalog of Urology Endoscopy Products (12 pages).
Olympus catalog of Urology Endoscopy Products (17 pages).
Smith, Cataneda-Zuniga Bronson, Article Titled "Endourology Principles and Practice", p. 113.
Richard Wolf catalog of Urology Endoscopy Products (24 pages).

* cited by examiner

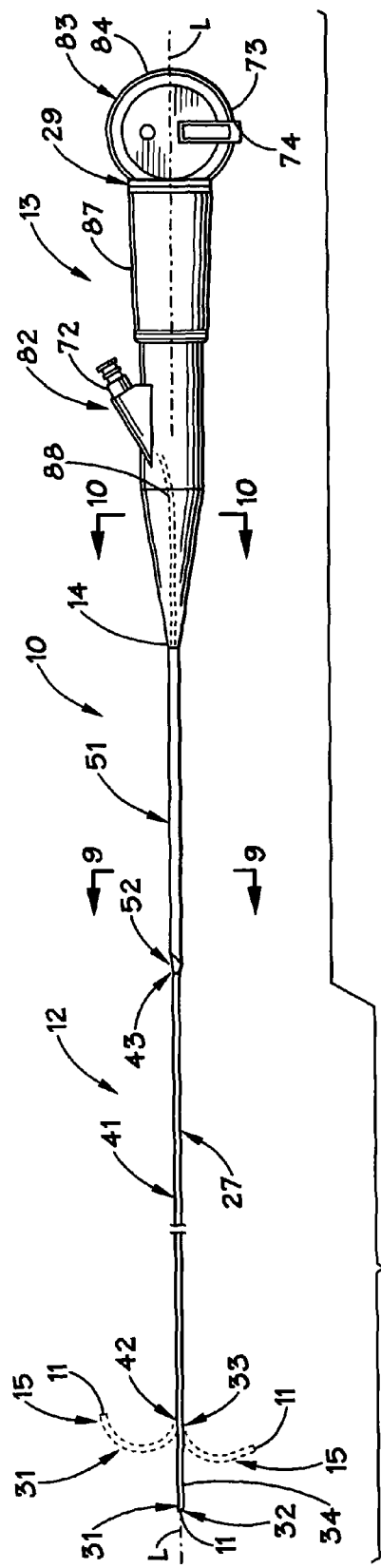
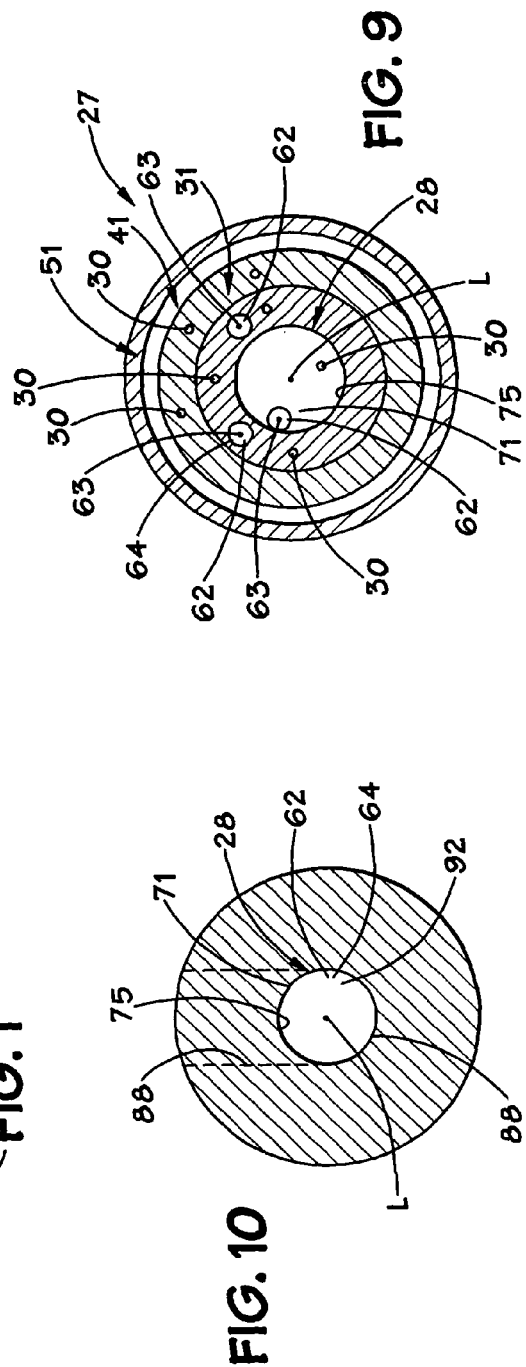
FIG. 1
FIG. 9
FIG. 10

SYSTEM, APPARATUS, AND METHOD FOR VIEWING A VISUALLY OBSCURED PORTION OF A CAVITY

RELATED APPLICATIONS

This application claims the benefit of U.S. Provisional Patent Application Ser. No. 60/464,602, filed Apr. 22, 2003.

BACKGROUND OF THE INVENTION

1. Field of the Invention

The invention relates to exploratory instruments and, more particularly, to endoscopic type instruments.

2. Description of the Related Art

Endoscopic type instruments have been developed to allow physicians and surgeons to view within a visually obscured portion of a body cavity. Physicians and surgeons in particular use endoscopic type instruments in a body to perform certain surgical procedures with limited trauma, disfiguration, expense, and hazards usually associated with conventional types of surgery performed through relatively large incisions.

Endoscopic type instruments may be constructed as rigid, semi-rigid, or flexible. Before the 1980's, segments of the urinary system such as the urethra, prostate and bladder were the anatomical areas that could only be examined and operated upon using substantially rigid endoscopes and/or conventional surgical procedure requiring large incisions. During the early 1980's, the introduction of new slimmer and longer endoscopes presented the field of urology with a major revolution by allowing the exploration of the ureter (the hollow tubular structure that leads the urine from the kidney to the urinary bladder) and upper urinary system within the kidney. These revolutionary instruments negated the need for a surgical procedure requiring a large incision. These new devices were named ureteroscopes and nephroscopes. Thus, the era of minimally invasive surgery had begun. These instruments were particularly helpful in removing kidney stones. Also, the advent of Extracorporeal Shock Wave Lithotripsy (stone fragmentation from outside of the body) made it necessary to dislodge and remove stone fragments from the kidney using an endoscopic type device in the ureter. During this time, the endoscopes were substantially rigid and their diameters were rather large, which had several limitations when entering and exploring a soft and curved conduit, such as the ureter.

Subsequently and towards the end of the 1980's, the incorporation of fiber optics into endoscopes permitted the reduction of the instrument's diameter and rendered the instrument's shaft some flexibility, thus overcoming "some" of the limitations of rigid endoscopes. This new generation of instruments were named "semi-rigid" miniscopes and made rigid scopes obsolete for most surgical procedures in the ureter and upper urinary tract, with the exception of percutaneous procedures in which rigid scopes are still used. These endoscopic type instruments, however, had many design and functionality limitations that do not facilitate diagnosis and surgery of body cavities, such as those in the upper urinary system. For example, rigid and semi-rigid endoscopes could not explore the upper urinary system within the kidney, thus, there was a risk of missing some pathology during diagnosis that might not be apparent by other imaging techniques such as x-rays, MRI, and CT scans, etc. Also, rigid and semi-rigid endoscopes were further inherently limited when performing surgical procedures that require flexibility.

By the end of the 1980's, "flexible" endoscopes were created to provide an opportunity to examine and operate on the upper urinary system. Currently, the semi-rigid and flexible endoscopes are the devices most commonly utilized for the ureter and upper urinary tract. The advantages of the flexible endoscopes are adaptability and finesse, or control of the device. The rigid, or even the semi-rigid, endoscopes do not permit exploration and intervention of the upper urinary tract within the kidney due to their inherent lack of adaptability and flexibility. For example, use of a rigid endoscope required penetration of the kidney during examination, or if entrance through the natural channels, then excessive rotation and maneuvering of the device is required, whereas the flexible endoscope has the versatility to maneuver through the urinary tract and directly into the kidney. Specifically, the rigid and semi-rigid endoscopes cannot properly explore the upper urinary system within the kidney; thus a diagnosis might be missed. Use of nonflexible endoscopes requires the surgeon to rotate the instrument to negotiate the passageways. The rigid and semi-rigid endoscopes are typically made of a hard material that can injure or lacerate the urinary system, if not used properly, especially during the rotating maneuver. Therefore, examination within the natural anatomical curves of the urinary system ideally requires use of flexible instruments that can adapt and maneuver through, and to, the ureter passage instead of forcing the ureter passage to adapt to the shape of the instrument.

Flexible endoscopes, however, are typically very difficult to use since their flexibility makes insertion of the instrument difficult, and proper use in such anatomical sections such as the upper urinary system is beyond the typical user's experience level. Most urologists do not have the skill, sensitivity, dexterity, or expertise to operate with fully flexible endoscopes. Fully flexible endoscopic type instruments are difficult to insert due to their lower consistency and firmness because they are typically made from a soft plastic, or polymer like material formed around the fiber optics, which material bends easily. Also, in addition to where the insertion end of the instrument bends, the flexible instruments are easily breakable at the union of the handle area and the instrument's shaft. The instrument's excessive flexibility makes handling difficult and often results in the need for an extra pair of trained hands, such as those of a nurse or physician, for its introduction. Because of its difficulty of use, most urologists prefer the rigid or semi-rigid endoscopes in spite of their limitations. Therefore, urologists have sought an endoscopic type instrument that: is surgically friendly; has reduced difficulty of use; should increase the probability of success, while minimizing the risks during surgery. Therefore, the art has also sought a new generation of endoscopes that will improve and facilitate surgery upon the urinary system (including the upper urinary tract within the kidney, bladder, prostate and urethra) and minimize the risk of laceration and injury during surgical procedures. More specifically, the art has sought an instrument design that: can facilitate the insertion of the instrument into, and through, a delicate non-linear cavity such as a urinary tract; facilitate the exploration of the upper urinary tract in order to diagnose and surgically intervene anywhere in the urinary system; provides stability to avoid breakage during the procedure; provides easier mobility within the upper urinary system; and facilitates the introduction of different accessories with more precision.

The design and elements of a traditional face tip of an endoscopic type instrument, either rigid, semi-rigid or flexible, has changed very little since the first one was introduced. Basically they all include one or more of the following input/output ports: a working channel port to introduce operating accessories to perform a procedure; an optical image collector-conductor port, for example, a telescope port for viewing;

a luminous conductor port, for example, an illumination fiberoptics port; and sometimes an irrigation & suction channel port. It is believed that with conventional endoscopes, the accessories are introduced before they can actually be observed within the urinary system. The conventional operating accessories exit port is located behind the optics created a "blind spot"; thus they enter the urinary system before the surgeon has visual control. In the medical setting, the exit of the accessories on the instrument's side is typically very close to the urinary tract wall. The surgeon's lack of view of the natural curves of the ureter, caused by the blind spot, can produce an inadvertent tear or perforation of the ureteral wall. Also, by exiting the operating tools on the side of the instrument, it obligates the surgeon to rotate the instrument in order to appropriately target the lesion, or the foreign body, to achieve the purpose of the exploration or the intervention. This maneuver, or "frequent rotation" may increase the risk of perforation and/or the inherent trauma by the instrument's insertion or pressure creating inflammation of the structures under exploration. Therefore, the art has sought an endoscopic type instrument wherein the working tool or accessories exit at the face tip, coincident with or in front of the viewing device to reduce the risk of laceration by allowing the surgeon to view the instrumental accessories as they exit either in front of the optics, lenses, or from the midsection of the instrument face tip Endoscopic type instruments have typically ranged in complexity from simple viewing scopes which employ a light source and an ocular system, to relatively complex instruments having a light source, an image collection system, fluid channels, and a surgical or working tool channel. The required features employed in an endoscopic type instrument are determined in part by the requirements of the type of examination or surgery in which the instrument is used.

The light source for illuminating the site of interest is usually positioned outside the cavity. The light is communicated through the instrument by an illumination, or light conductor, usually formed of a fiber optic bundle. It is conceivable that the light conductor could be separate from the instrument itself. This would allow for use of an endoscope with a reduced diameter or would allow additional functions in a scope of a given diameter. No matter what additional use endoscopic type instruments have been put to, their examination properties remain their staple use. Conventional lenses for image collection and transmission generally require that the instrument be rigid or semi-rigid. Flexible endoscopic type instruments typically employ coherent optical fiber bundles wherein the opposite ends of the fibers are identically ordered. The image quality of lens based image collection and transmission is generally superior to image collection and transmission formed of fiber optics or fiber optics alone.

Endoscopic type instruments may be constructed to have fluid channels which may serve a variety of different purposes. For example, in certain procedures on the lungs, the fluid channel provides an air passage to allow the lung to breathe. In other procedures, the fluid channel may be used to insufflate, or inflate, a cavity in the body for better access to obtain a better view. In other procedures, a supply of cleansing fluid, such as water, may be used to clear away undesirable contaminant fluid, such as blood, from a location to facilitate inspection or to clean the image collector. A suction line is often used for removing fluids from the site. A working tool channel provides for the insertion of various working implements, or accessories, through the instrument such as forceps, scissors, punches, electrodes, lasers, and the like.

An endoscopic type instrument may include a typically tubular shaped shaft connected to a handle and viewing assembly which typically provide a mechanical coupling to which a viewing apparatus is connected. The typical endoscopic type instrument may include fluid channels extending through the shaft which communicate with external fluid connections on the handle and the assembly. A working tool port on the handle and viewing assembly typically communicates with a working tool channel in the shaft and may include a clamp or other support device to hold the working tool in place. An illumination port typically communicates with a light source. The light is normally transmitted from the viewing end or proximal end of the instrument to a light directing lens, or lenses, at the distal end. An optical collector including an objective lens is positioned at the distal end and passes the image through the image conductor to the handle and viewing apparatus through which the operator views the section of the cavity of interest. The objective lens, if used, is typically fixed and may be oriented along the longitudinal axis of the shaft or be angled off-axis for a view to the side. Some endoscopic type instruments have a fixed combination of functions, while others may be adapted to allow a selection of functions from a variety of working tools and viewing methodologies.

The handle and viewing apparatus of endoscopic type instruments usually accommodate various adapters for connecting various types of video, or other imaging, devices. In some cases, an image multiplexer is utilized to separate the image for simultaneous display on an optical viewer used for direct viewing and a video imager to televise or record the procedure.

An endoscopic type instrument having only a single optical collector-optical conductor or single telescope, alone, creates only a two-dimensional, or monoscopic, view of the region under inspection. This often results in a lack of depth perception for the user of the instrument, making it difficult to perform an accurate inspection or surgery. Three dimensional, or 3-D, viewing would allow for more precise viewing when maneuvering inside such anatomical features as the urinary tract, and would allow for better identification and perception of dimensions and distances from the instrument tip to the object in question, especially where the instrument is being used in a cavity containing a fluid. Although, three-dimensional, or stereoscopic, laproscopic type instruments, such as steromicroscopes, have been developed for creating a three-dimensional view of the object or region under inspection these are not suited for use in endoscopics. These instruments are provided with a pair of optical pathways or channels for transmitting a plurality of simultaneously gathered images of the object of interest to a stereoscopic viewer. Traditionally, the stereoscopic viewer has had microscope-like eyepieces through which the viewer views the respective images. The eyepieces are arranged so that the viewer's eyes provide the necessary convergence to combine the images into a stereoscopic view. Convergence of right eye and left eye images of an object is done in normal stereopsis by converging the optical axes with the eyes or optical/mechanical means to accomplish convergence of the right and left images so that the brain receives and perceives the images as sufficiently close together for the brain to combine the images as a single three-dimensional image. The stereomicroscope is an example of such an optical/mechanical device. Although the human brain can converge and "fuse" two separate views if the separation between the images is not too great, this is not easy or comfortable to achieve in practice. In typical stereomicroscopes, the problem is solved by using two converging optical systems. However, this is not a practical solution in endoscopic type systems where the necessary convergence at very short focal lengths is compounded by the need to keep the overall diameter of the system as small as possible so that the endoscope tube can be inserted through a single minimum size surgical incision, minimizing invasive procedures. Also, traditionally, where a video viewing system is used, the two parallel optical systems used in such arrangements do not converge the images and provide two separate images or video pictures.

Accordingly, prior to the development of the present invention, it is believed that there has been no endoscopic type instrument which: has the versatility of a flexible endoscope, while retaining the controllability of a semi-rigid or rigid endoscope; has an instrument shaft which is both rigid for a portion of its length and flexible for a portion of its length; which avoids, or reduces, the necessity for rotation of the instrument when targeting is required and while working inside delicate cavities; provides three dimensional imaging; does not have a blind spot associated with the instrument when working tools or accessories exit the instrument. Therefore, the art has sought an endoscopic instrument, or endoscope, which has the versatility of a flexible endoscope, while retaining the controllability of a semi-rigid or rigid endoscope; has an instrument shaft which has a rigid portion and a flexible portion; prevents, or reduces, the necessity for rotation of the instrument when targeting is required and while working inside delicate cavities; provides three dimensional imaging in the viewing system; and does not have a blind spot at the point where the working tools or accessories exit the instrument.

SUMMARY OF THE INVENTION

In accordance with the invention the foregoing advantages have been believed to be achieved through the endoscope, endoscope system, and method for viewing a portion of a body cavity of the present invention. The endoscope system of the present invention for viewing a visually obscured portion of a body cavity may include: an endoscope have a face tip assembly, having a plurality of input/output ports, associated with a shaft assembly, the shaft assembly being associated with a handle and viewing assembly; the shaft assembly including a shaft having a distal end and an actively flexible shaft segment disposed at the distal end of the shaft for insertion into the cavity; a least one optical image collector adapted to gather an image from within the body cavity; at least one optical conductor, associated with the at least one optical image collector, and adapted to transmit the image to the handle and viewing assembly; at least one luminous conductor adapted to provide illumination to the body cavity; at least one working channel disposed within the shaft assembly adapted to permit a working instrument entry into the body cavity; and an imaging apparatus, associated with the at least one optical conductor, and adapted to capture the image to send it to a human interface apparatus adapted to permit viewing of the image.

Another feature of this aspect of the invention is that the endoscope system may include a working channel extension, associated with the face tip assembly, which includes at least one protrusion adapted to guide the working instrument and to prevent impact of foreign matter located within the body cavity upon the at least one optical collector. An additional feature of this aspect of the present invention is that there may be two optical conductors for producing a three-dimensional image. A further feature of this aspect of the present invention is that the actively flexible shaft segment may be disposed adjacent a passively flexible shaft segment. An additional feature is that the passively flexible shaft segment may be disposed adjacent a semi-rigid shaft segment.

In accordance with the invention, the foregoing advantages have also been achieved through the present endoscope for viewing a portion of a body cavity. This aspect of the present invention may include: a face tip assembly, have a plurality of input/output ports, associated with a shaft assembly, the shaft assembly being associated with a handle and viewing assembly; the shaft assembly may include a longitudinal axis, a shaft having a distal end and an actively flexible shaft segment disposed at the distal end of the shaft for insertion into the body cavity; at least one optical image collector adapted to gather an image from within the body cavity; at least one optical conductor, associated with the at least one optical image collector, and adapted to transmit the image to the handle and viewing assembly; at least one luminous conductor adapted to provide illumination to the body cavity; and at least one working channel disposed within the shaft assembly and adapted to permit a working instrument entry into the body cavity.

An additional feature of this aspect of the present invention is that the endoscope may include a working channel extension associated with the face tip assembly, which includes at least one protrusion to guide the working instrument and to prevent impact of foreign matter upon the at least one optical image collector. A further feature of this aspect of the present invention is that the shaft assembly may have a longitudinal axis and the at least one optical image collector may lie in a first plane which is disposed substantially perpendicular to the longitudinal axis of the shaft assembly; and the at least one protrusion is disposed at the distal end of the shaft forward of the first plane in which the at least one optical image collector lies, whereby the at least one optical image collector may view an operating tool passing forwardly beyond the at least one protrusion.

Another feature of this aspect of the present invention is that the plurality of input/output ports may include at least one operating tool port, and the operating tool port lies in a second plane which is disposed substantially parallel with the first plane in which the at least one optical collector lies. The first plane and the second plane may be substantially coplanar or the second plane be disposed in a spaced relationship from the first plane, toward the distal end of the shaft.

BRIEF DESCRIPTION OF THE DRAWINGS

While some of the features, advantages, and benefits of the present invention, having been stated, others will become apparent as the description proceeds when taken in conjunction with the accompanying drawings in which:

FIG. 1 is a side view of an endoscope, such as a ureterscope, in accordance with the present invention;

FIG. 9 is a partial cross-sectional view of the endoscope of FIG. 1, taken along line 9-9 in FIG. 1;

FIG. 10 is a partial cross-sectional view of the endoscope of FIG. 1, taken along line 10-10 in FIG. 1.

Figure 2:
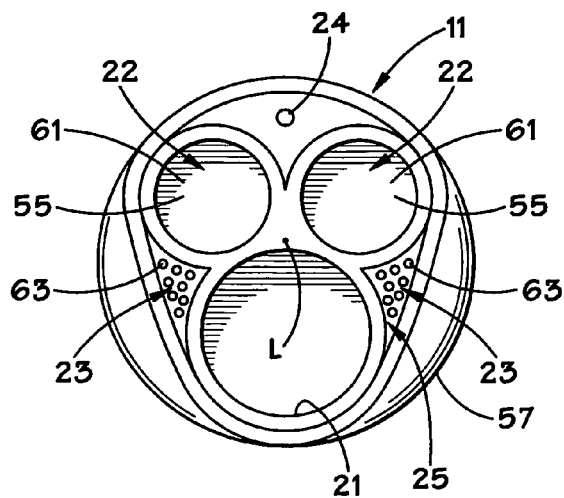
FIG. 2 is a front view of a face tip assembly for use with the endoscope of FIG. 1.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE PREFERRED EMBODIMENT

The present invention will now be described more fully hereinafter with reference to the accompanying drawings which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like reference numbers refer to like elements throughout, and the prime notation, if used, indicates similar elements in alternative embodiments. The preferred embodiment of the present invention implements an endoscopic type instrument, or endoscope, which may be in the form of a ureteroscope.

Referring now to the drawings, a first embodiment of the present invention in the form of a ureteroscope 10 is illustrated in FIGS. 1-4. This ureteroscope 10 is only one of many variations of endoscopes, or endoscopic type instruments, that can be produced using the teachings of the present invention. The preferred embodiment of a ureteroscope 10 of the present invention generally comprises: a face tip assembly 11 connected to a shaft, or shaft assembly 12, the shaft assembly 12 being connected to, or associated with, a handle and viewing assembly 13. In conjunction with the face tip assembly 11, the shaft assembly 12 provides for a reduced risk of laceration of a cavity by allowing the use, or viewing, of conventional, instrument accessories, or "operating tools" (not shown), by providing a tool exit, or port 21, in front of an optical image collector 61, FIGS. 2 and 5, or an exit, or port 21', in the center of the face tip assembly 11, FIG. 7. The shaft assembly 12 also: provides for simultaneous usage of both the viewing apparatus and an operating tool; facilitates exploration in such cavities as the upper urinary tract; and avoids the necessity for excessive rotation of instruments when targeting, or viewing, is required while working inside such sensitive cavities such as the ureter.

Figure 3:
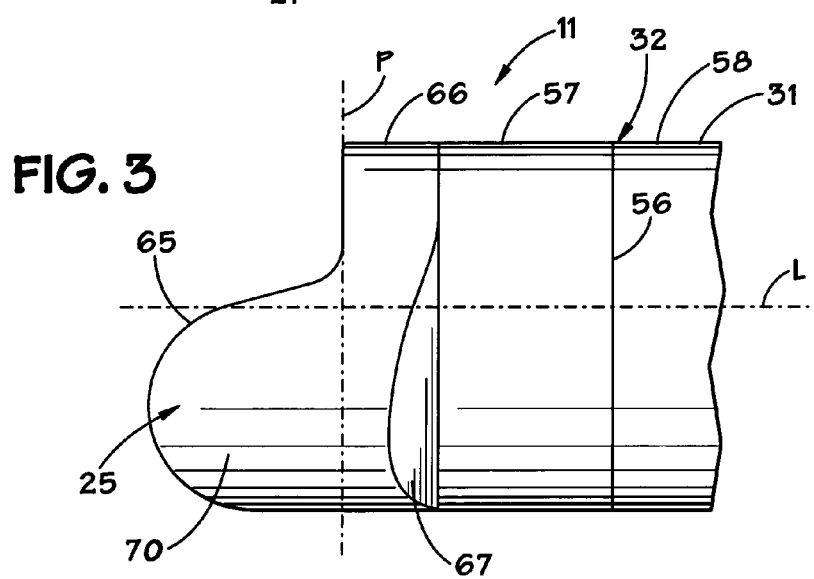
FIG. 3 is a side view of the face tip assembly of FIG. 2.
Figure 4:
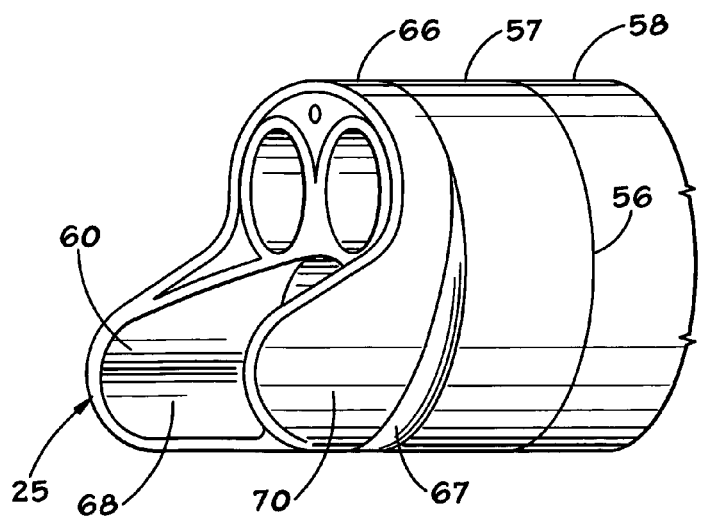
FIG. 4 is a perspective view of the face tip assembly of FIGS. 2 and 3.

Referring now to FIGS. 2-4, an embodiment of face tip assembly 11 includes a plurality of input/output ports. The ports may include: an operating tool port, or tool exit, 21 where conventional operating accessories (not shown) may exit and are introduced; at least one optical image channel port 22, and at least one luminous channel port 23. The face tip assembly 11 may also include at least one fluid and/or suction channel port 24. The face tip assembly 11 also includes at least one optical image collector 61 interfaced with the at least one optical image channel port 22 of face tip assembly 11, for gathering an image from within the interior body cavity. The type of optical image collector 61 corresponds with the type of optical conductor 62 utilized in ureteroscope 10. For example, selection of an optical waveguide to implement the optical conductor 62 may result in the requirement for a lens, or prism, as an optical image collector 61. If the means for implementing the optical conductor 62 utilized is fiber optics, such as a fiber optics bundle or array, the face of the fiber-optics array may, in turn, be the only means required to collect the optical image for transmission through the optical conductor 62 through to the handle and viewing assembly 13, albeit, with reduced visual acuity. The face tip assembly design, of FIGS. 2-4, as well as other designs hereinafter described, provide the mobility to access the upper urinary system within the kidney and incorporate improved visibility so as to avoid the "blind spot" inherent in many systems comprising the state-of-the-art.

A preferred embodiment of the face tip assembly 11 is best shown in FIGS. 2-4, as a three-dimensional viewing face tip design. In this embodiment, the face tip assembly 11 is a separate unit associated with, or connected to, the distal end 32 of a first flexible shaft segment 31 of shaft assembly 12. In this embodiment, where the distal end 32 has a substantially circular cross-sectional shape, the face tip assembly 11 is "face shaped", or appears as having two eyes and a mouth, as shown in FIG. 2. The face tip assembly 11 includes a plurality of optical image collectors 61, which, in this embodiment take the form of a pair of lenses 55 which provide for a three-dimensional view. The lenses 55 are preferably positioned in a plane P disposed substantially perpendicular to the longitudinal L axis of shaft segment 31 and shaft assembly 12 and face assembly 11 (as shown in FIG. 3). Plane P may also be considered to be disposed substantially parallel to the interface 56 between face tip assembly 11 and the distal end 32 of flexible segment 31 of shaft assembly 12. As illustrated, the two lenses are preferably spaced upwardly of the longitudinal axis L. In this embodiment, face tip assembly 11 also includes an operating tool port 21 which is preferably offset from the center of the face tip assembly 11, or longitudinal axis L, away from the lenses 55, toward the outer perimeter 57, of face tip assembly 11. In this embodiment, the face tip assembly's 11 outer perimeter 57 may be partially congruent with the outer perimeter 58 of the distal end 32 of the first flexible shaft segment 31. In this embodiment, luminous conductors 63 for light conduction and illumination, in the form of a fiber optics bundle, array, or a single fiber optic strand is located in a portion of the spaces between the lenses 55 and operating tool port 21, as shown in FIG. 2.

As shown in FIGS. 3 and 4, face tip assembly 11 may have a working channel port extension 25 which may be in the form of at least one protrusion 65 which functions as an operating tool guide that tends to restrict movement of the operating tool to movement generally along longitudinal axis L. As an operating tool (not shown) exits from operating tool, or tool, port 21, the protrusion 65 may act as a guide to prevent the operating tool from moving outwardly toward the adjacent wall surface of an adjacent body passageway (not shown) until after the end of tool is visible to the operator via lenses 55. Additionally, protrusion 65 provides protection of the lenses 55 from impact with particulate matter (stone fragments, etc.). The protrusion 65 may be formed integrally as a unitary structure with the outer perimeter 57 of face tip assembly 11. The protrusion 65 may have two spaced apart peaks 60, 70 extending forwardly toward a distal end of the face tip assembly and from a smooth rounded outer distal surface 66. The peaks 60, 70 may preferably be disposed adjacent each side of the tool port 21, as shown in FIGS. 2-4. In this embodiment, where the protrusion 65 is formed as a unitary structure, the protrusion 65 has a concave proximal deflection 67 adjacent outer perimeter 57 in a spaced relationship from interface 56. Alternatively, the working channel port extension 25 may be a separate structure connected to the front of face tip assembly 11. Although the working channel port extension 25 shown in FIGS. 3-4 is a unitary structure with a smooth rounded outer distal surface 66 and a smooth inner surface 68 smoothly contoured and tapering toward operating tool port 21, one of ordinary skill in the art would understand there are many variations of positioning the working channel port extension 25 within the spirit and scope of the present invention. Preferably, as shown in FIGS. 3, 4, and 6, the peaks 60, 70 are disposed offset from the center of the face tip assemblies 11, 11', or longitudinal axis L, and are disposed with a substantial portion of peaks 60, 70 disposed below longitudinal axis L.

Additionally, although the operating tool port 21, lenses 55, and the distal end 32 of first flexible segment 31 are depicted as having generally, circular cross-sectional configurations for the preferred embodiment, it is important to note that in variations of this embodiment, other geometric shapes as known by those of ordinary skill in the art, are within the spirit of the disclosure, such as elliptical, oval, or other shapes. Also, still within the spirit of the preferred embodiment, the distal end 32 of first flexible segment 31 may have a smaller circumference, or diameter, than the main shaft body 34 of first flexible shaft segment 31, whereby the outer perimeter 57 of face tip assembly 11 may be at least partially received around, and connected to, the smaller outer circumference of distal end 32. Still referring to FIGS. 2-4, face tip assembly 11, may include variations in the shape of outer perimeter 57, variations in the positioning, or location, of lenses 55, operating tool port 21, and optical conductor 62. Additionally, in other embodiments of the face tip assembly 11 structure depicted in FIGS. 2-4, the optical image collector 61 may be in another form such as prisms or a substantially flush bundle of fiber optics or other methodologies as known by those of ordinary skill in the art. The optical conductor 62 and luminous conductors 63 may also be in any acceptable form as known by those of ordinary skill in the art that can perform substantially the same function as fiber optics.

Figure 5:
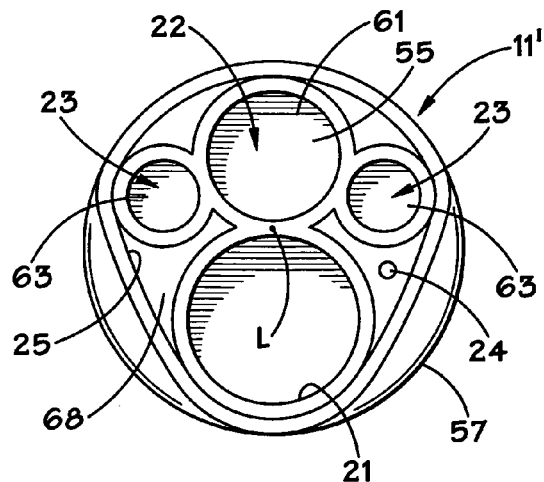
FIG. 5 is a front view of another embodiment of a face tip assembly for use with the endoscope of FIG. 1.
Figure 6:
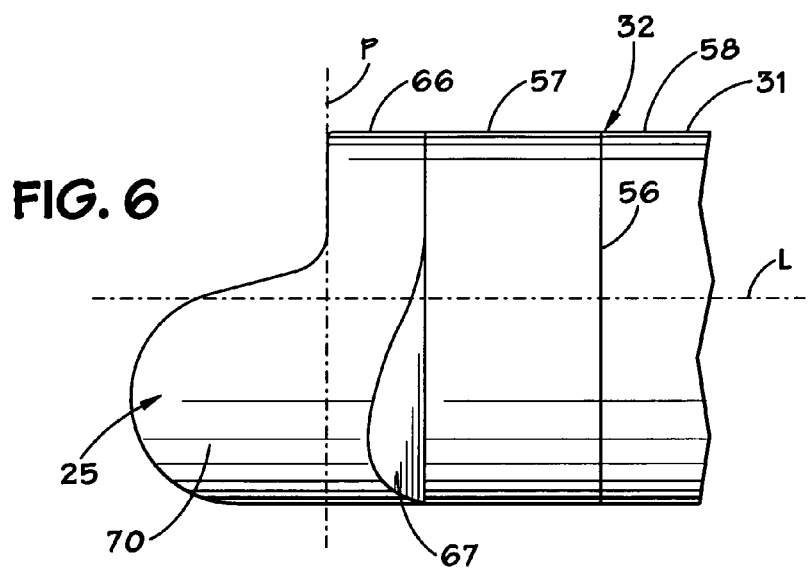
FIG. 6 is a side view of the face tip assembly of FIG. 5.

Referring now to FIGS. 5-6, a monoptic face-tip assembly embodiment is illustrated. In this face tip assembly 11', the general shape of the outer circumference 57 and protrusion 65 are substantially similar to those described in connection with FIGS. 2-4. In this embodiment, the face tip assembly 11' is a separate unit connected to the distal end 32 of first flexible shaft segment 31. In this embodiment, when the distal end 32 has a substantially circular cross-sectional configuration, the face tip assembly 11' may have a corresponding generally, circular cross-sectional configuration shown in FIG. 5. The face tip assembly 11 includes a single optical image collector 61, which, in this embodiment takes the form of a single lens 55 which provides for a view to help those users with difficulty in adapting to three-dimensional viewing. The lens 55 is positioned, or disposed, on plane P and spaced from longitudinal axis L, and offset toward the outer perimeter 57. In this embodiment, the face tip assembly 11' also includes an operating tool port 21 which is offset from the center, or longitudinal axis L, of the face tip assembly 11', away from the lens 55, toward the outer perimeter 57 opposite that of lens 55. In this embodiment, outer perimeter 57 of face top assembly 11', is partially congruent with the outer perimeter 58 of the distal end 32 of the first flexible segment 31. Luminous conductors 63 for light conduction and illumination in the form of fiber optics may be located on opposite sides of the lens 55. In this embodiment, face tip assembly 11' also has a working channel port extension 25 in the form of the protrusion 65, previously described, which may function as an operating tool guide as previously described, and provides protection of the lens 55 from impact with particulate matter (stone fragments, etc.). In this embodiment, the protrusion 65 is again formed integrally as a unitary structure with the outer perimeter 57 of face tip assembly 11'. The protrusion 65 has two peaks 69, 70, formed by smooth rounded outer distal surface 66. In this embodiment, when the protrusion 65 is formed of a unitary structure, the protrusion 65 also may have a concave proximal deflection 67, spaced from interface 56. The working channel port extension 25 may be a separate structure connected to the front of face tip assembly 11'.

Although the working channel port extension 25 is shown in FIGS. 5-6 as a unitary structure extending forwardly from a smooth rounded outer distal surface 66 and a smooth inner surface 68 smoothly contoured and tapering toward operating tool port 21. One of ordinary skill in the art would understand there are many variations of positioning the working channel port extension 25 within the spirit of the disclosure. Additionally, although the operating tool port 21, lens 55, and the distal end 32 of first flexible shaft segment 31 are depicted as having generally circular shapes for this embodiment, in variations of this embodiment, other geometric designs, or shapes, as known by those of ordinary skill in the art, are within the scope of the present invention. Again, the distal end 32 of first flexible segment 31 may have a smaller circumference than the main shaft body 34 of first flexible shaft segment 31, whereby the outer perimeter 57 of face tip assembly 11 may be at least partially received around, and connected to the smaller outer circumference of distal end 32. Still referring to FIGS. 5-6, there may be variations in the shape of outer perimeter 57, variations in the positioning of lens 55, operating tool port 21, and optical conductors 62. Again, the optical image collector 61 may be in another form such as prisms or a substantially flush bundle of fiber optics or other methodologies as known by those of ordinary skill in the art. The optical conductor 62 and luminous conductors 63 may also be in any acceptable form as known by those of ordinary skill in the art that can perform substantially the same function as fiber optics. The protrusion 65 in the embodiments discussed regarding FIGS. 2-4 and FIGS. 5-6 may be in more of a form similar to a semicircular hollow cylinder of a more equal distal height as opposed to a form similar to peaks and valleys as described above, as well as may have the other shapes which provide the desired tool guiding functions.

Figure 7:
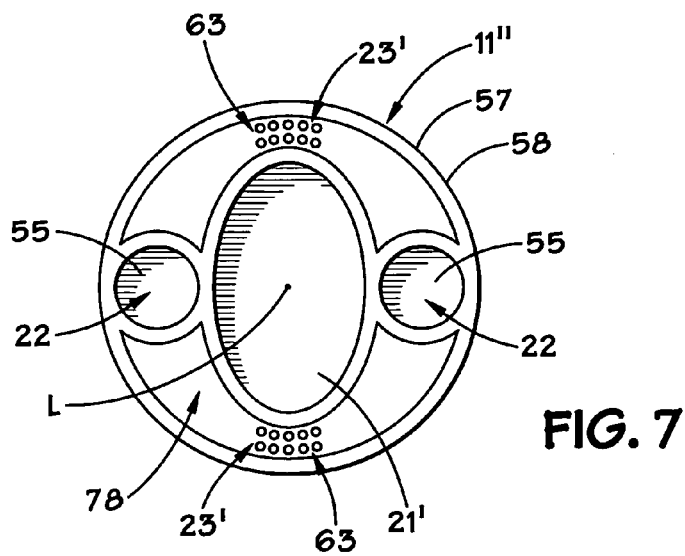
FIG. 7 is a front view of another embodiment of a face tip assembly for use with the endoscope of FIG. 1.

With reference to FIG. 7, an alternative three-dimensional viewing face-tip assembly 11" is shown. The face tip assembly 11", generally has the shape of the face of face tip assemblies 11 and 11', but is generally flatter in appearance, and lacks substantial protrusions 65. In other words, the front face 78 of face tip assembly 11" generally lies in a plane substantially parallel with plane P previously described. The face tip assembly 11" may also include a generally elliptical shaped operating tool port 21' which is substantially centered between the lenses 55. Disposed on either side of port 21' plurality of optical image collectors 61, which, in this embodiment may take the form of a pair of lenses 55 which provide for a three-dimensional view. The lenses 55 are generally positioned on a plane substantially parallel with plane P previously described.

Still with reference to FIG. 7, the outer perimeter 57 of face tip assembly 11" is generally congruent with the outer perimeter 58 of the distal end 32 of the first flexible shaft segment 31. In this embodiment, luminous conductors 63 for light conduction and illumination in the form of fiber optics as previously described, may be positioned above and below the elliptical shaped port 21'. Although the operating tool port 21' is depicted as generally elliptical, and lenses 55 and the distal end 32 of first flexible segment 31 are depicted as circular for this embodiment, it is important to note that in variations of this embodiment, other geometric designs and shapes, as known by those of ordinary skill in the art, are within the scope of the present invention. Also, still within the spirit of this embodiment, the distal end 32 of first flexible shaft segment 31 may have a smaller circumference than the main shaft body 34 of first flexible shaft segment 31, whereby the outer perimeter 57 of face tip assembly 11 may be at least partially received around, and connected to, the smaller outer circumference of distal end 32. Still referring to FIG. 7, another embodiment may include variations in the shape of outer perimeter 57, variations in the positioning of lenses 55, operating tool port 21', and optical conductor 63. Additionally, in other embodiments of the face tip assembly 11' structure depicted in FIG. 7, the optical image collector 61 may be in another form such as prisms or a substantially flush bundle of fiber optics or other methodologies as known by those of ordinary skill in the art. The optical conductor 62 and luminous conductors 63 may also be in any acceptable form as known by those of ordinary skill in the art that can perform substantially the same function as fiber optics.

Figure 8:
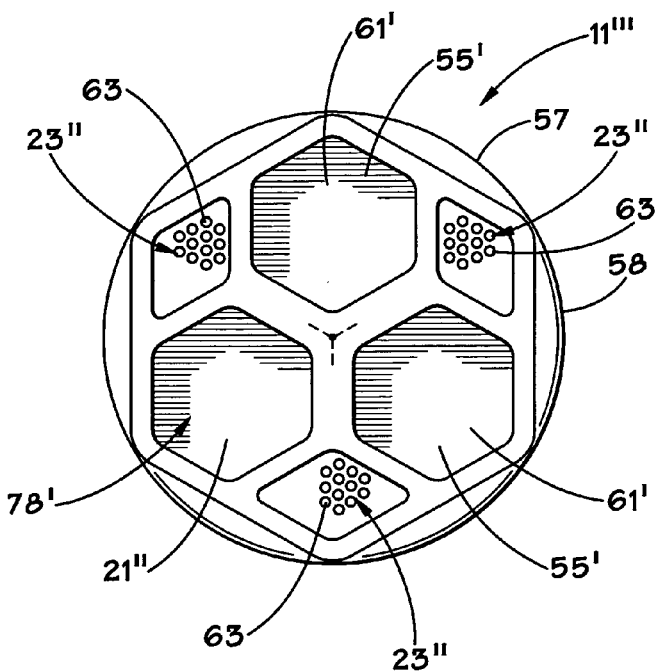
FIG. 8 is a front view of another embodiment of a face tip assembly for use with the endoscope of FIG. 1.

Referring now to FIG. 8, another alternative three-dimensional viewing face-tip assembly 11''' is shown. In this face tip assembly 111''', the general shape of the face 78' of face tip assembly 11''' is flatter in appearance than those described in FIGS. 2-4 and FIGS. 5-6 and thus lacks a substantial protrusion 25 formed by peaks 69, 70. Front face 78' also generally lies in a plane substantially parallel with plane P previously described. The face tip assembly 111''' may include a pair of optical image collectors 61', which, in this embodiment take the form of a plurality of hexagonal shaped lenses 55' which provide for a three-dimensional view. The lenses 55' are positioned in plane P, as previously described and are offset toward the outer perimeter 57. In this embodiment, the face tip assembly 11''' also includes an operating tool port 21" which is offset from the center, or longitudinal axis L, of the face tip assembly 11''', away from the lenses 55', toward the outer perimeter 57. In this embodiment, luminous conductors 63 for light conduction and illumination in the form of fiber optics are disposed in luminous channel ports 23" located circumferentially between the lenses 55' and between lenses 55' and operating tool port 21" and form a generally triangular shaped array wherein each port 23" is located at the tips of the triangle. In this embodiment, face tip assembly 11 has a hexagonal shape and connects with, or alternatively is a part of, the first flexible shaft segment 31. Although the operating tool port 21" and lenses 55' are hexagonal shaped, luminous channel ports 23" is diamond shaped, and the distal end 32 of first flexible shaft segment 31 is depicted as circular, it is important to note that variations of this embodiment, would permit other geometric designs as known by those of ordinary skill in the art, within the scope of the invention. Also, the distal end 32 of first flexible shaft segment 31 may be in the shape of a hexagon and have a smaller circumference than the main body 34 of first flexible shaft segment 31 whereby the outer perimeter 57 of face tip assembly 11''' may be at least partially received around, and connected to, the smaller outer perimeter of distal end 32. Still referring to FIG. 8, another embodiment may include variations in the shape of outer perimeter 57, variations in the positioning of lenses 55", operating tool port 21", and fiber-optic optical conductor 62. Additionally, in other embodiments of the face tip assembly 11''' depicted in FIG. 8, the optical image collector 61' may be in another form such as a prism or a substantially flush bundle of fiber optics or other methodologies as known by those of ordinary skill in the art. The optical conductor 62 and luminous conductors 63 may also be in any acceptable form as known by those of ordinary skill in the art that can perform substantially the same function as fiber optics.

Referring to FIGS. 1 and 9, the shaft assembly 12 of ureteroscope, or endoscope, 10 includes a shaft 27 having at least one longitudinally extending passageway 28 and handle and viewing assembly interface 29. Preferably, there is a passageway 28 which corresponds to, and is in communication with, each operating tool port 21-21", optical image channel port 22, 22', and luminous channel port 22-23". The shaft 27 is preferably constructed of a suitable nontoxic material, such as a plastic or polymer material and includes a first flexible shaft segment 31 having distal end 32 adapted for insertion into the cavity and interfaced with the face tip assembly 11 at interface 56; a second flexible shaft segment 41 having a distal end 42 connected to a proximal end 33 of the first flexible shaft segment 31; and a third shaft segment 51 having a distal end 52 connected to a proximal end 43 of the second flexible shaft segment 41.

Preferably, the shaft 27 is constructed so that it has a substantially smooth, continuous outer surface, and its preferred cross-sectional configuration is circular. Preferably the length of the third shaft segment 51 is approximately 50 cm long. The first flexible shaft section 31 is preferably approximately 4 cm long, and the second flexible shaft section 41 is preferably approximately 20 cm long. The first and second flexible shaft sections 31, 41 preferably have cross-sectional configurations that are substantially uniform along their lengths, but they may taper downwardly toward the face tip assembly 11. The third section 51 of shaft 27 is constructed so that it has sufficient strength and rigidity to permit use within the bladder and to support the entry of the first and second flexible sections 31, 41 into the ureter and may be described as rigid or semi-rigid in construction. The first and second flexible shaft sections 31, 41 are constructed in order to follow the contours of the ureter. Also, as is known by those of ordinary skill in the art of endoscopes, the lengths of the first segment 31, second segment 41, and third segment 51 of the shaft 27 may vary according to the intended use of the endoscope 10.

The third shaft segment 51 is dimensioned to be received in a human body so that it extends through the urethra and substantially through the bladder, The distal end 52 of segment 51 is tapered to receive the proximal end 43 of the second flexible segment 41 and is formed to provide a smooth, gradual transition between the second flexible segment 41 and the third segment 51, to permit the non-traumatic passage of the shaft 27 through the urethra and into the bladder. Preferably, the third section 51, preferably, has sufficient strength and rigidity to enable both axial and rotational translation with the maneuvering of the handle and viewing assembly 13, without excessive twisting of the shaft 27. Additionally, the connection 14 between shaft segment 51 and the handle and viewing assembly 13 has sufficient strength and rigidity to avoid breaking during use and handling of endoscope 10. Thus, the user is able to insert the shaft 27, leading with face tip assembly 11, into the urethra and maneuver the instrument through the bladder in order to position the first flexible section 31 and thus the face tip assembly 11 into the opening of the ureter. The first flexible segment 31 having distal end 32 adapted for insertion into the cavity is dimensioned to be received in the ureter of a patient.

The second flexible shaft segment 41 having a distal end 42, like first flexible shaft t 31 is correspondingly also dimensioned to be received in the ureter of a patient and is sufficiently flexible along its length to follow various canals of the human body, such as the ureter. In order to optimize the versatility of a flexible endoscope while retaining the controllability of a rigid endoscope, the second flexible segment 41 is "passively flexible". The term "passively flexible" is intended to mean that shaft segment 41 may be moved, flexed, or bent, to assume a curved configuration, in response to forces exerted upon the shaft 27 as it passes through a cavity or body passageway, but the movement, flexing, or bending is not substantially controllable by the operator of the instrument. While the third shaft segment 51 provides the user with sufficient feel and control of the instrument 10, the second flexible segment 41 has the ability to readily flex and follow the contours of a cavity or passageway, such as the ureter, without excessive deformation of its cavity or passageway, in order to minimize any traumatic effects.

In contrast, the first flexible shaft segment 31 is "actively flexible". The term "actively flexible" is intended to mean that shaft segment 31 may be moved, flexed, or bent to assume a curved configuration, such as shown in phantom lines 15 in FIG. 1, or an angular disposition with respect to longitudinal axis L, and such movement, flexing or bending is substantially controlled by the operator, who can cause and control the desired movement, flexing, and/or bending. The deflection of face tip assembly 11 upon operator, or user, command, or control, aids the user in the detection and penetration of the opening of the ureter. Additionally, the relatively small diameters of face tip assembly 11 and first flexible shaft segment 31 allow the user to insert the shaft 27 into the narrow opening of the ureter to gain access to the ureter and kidney. The active flexibility of the first flexible shaft segment 31 also provides for non-traumatic use of the instrument 10 and precise positioning of the face tip assembly 11 adjacent to items of interest such as a lesion or kidney stone. Most significantly, the actively flexible first flexible segment 31 enables the user to view and, along with other features of the present invention, non-traumatically deliver a working tool via the working channel 71 and operating tool port 21 to the item of interest. The flexibility of the first flexible segment 31 generally negates the need for rotating the instrument when targeting or advancing the instrument as required.

The first flexible shaft segment 31 may be made actively flexible using various methodologies. In the preferred embodiment, the first flexible segment 31 is made actively flexible through use of operating, or guide, wires 30 guided through individual conduits which pass longitudinally through shaft segment 31 or a through passageway 28 within shaft 27 toward the distal end 32, which wire, or wires, may be manipulated, or pulled, so as to bend, move, or flex, the shaft segment 31 in a desired direction. The distal ends of the wires 30 may be suitably anchored adjacent he distal end 32 of shaft segment 31, whereby upon pulling on the wire, or wires 30, the desired controlled flexing, moving, or bending will occur. Alternatively, the first flexible shaft segment 31 may be comprised of a connected string of body members consisting of semicircular disc-like ring elements forming selectively controllable expandable bodies, whereby upon controlled expansion of selected ring elements, the shaft segment 31 moves or flexes in the desired direction, similar to the manner in which a snake moves. Other methodologies for providing the requisite flexibility could include the use of springs, separate wire guides, or the working tool itself, among others. If desired, the cross-sectional shape of first flexible shaft segment 31 could be varied in order to provide varying inherent flexibility characteristics. In other words, one or more portions, or sides, of the first flexible shaft segment 31 can be made to be more pliable, or flexible, than other portions, or sides, of the same first flexible shaft segment in order to make a shaft segment that more readily flexes in a first direction and is more rigid in a second direction.

Alternatively, the first flexible shaft segment 31 can be made from a composite material that has differing properties that will result in having a first flexible segment 31 predisposed to more readily bend, or flex, in a first direction, for example, upwardly and downwardly, rather than from side to side. Alternatively, the active desired flexibility of the first flexible shaft segment 31 could be obtained by use of a longitudinally disposed tension cable with a distal spring deflection recovery member, whereby increased tension or compression on the tension cable initiated through a suitable control causes the flexible shaft segment 31 to deflect or flex in a desired direction.

Face tip assemblies 11, 11', 11", 11''' may be a separate multi-port piece which is connected to the distal end 32 of first flexible shaft segment 31 of shaft 27 as previously described. In an alternative embodiment, the face tip assemblies 11-11''' may be a unitary piece formed integral with first flexible segment 31 as previously described. If desired, the same material used to form the first flexible shaft segment 31 may also be used for the second flexible shaft segment 41. The first flexible shaft segment 31 may have approximately the same diameter as the second flexible shaft segment 41, and the two segments may be formed integral with each other or formed separately and connected by any suitable connection. If desired, as seen in FIGS. 1 and 9, the first shaft segment 31 could extend along the longitudinal axis L of the shaft 27 from its distal end 32 to the handle and viewing assembly, whereby shaft segment 31 is concentrically disposed within the second shaft segment 41 and third shaft segment 51. In turn, the second shaft segment could also extend along the longitudinal axis L of shaft 27 to the handle and viewing assembly 13, whereby shaft segment 41 is concentrically disposed within the third shaft segment 51. Where the first shaft segment 31 enters the second shaft segment 41, and where the second shaft segment 41 enters the third shaft segment 51, define transition zones, or transition locations, 39, 49, and preferably at these zones the larger diameter shaft segment as shown at zone 49 in FIG. 1. These tapering transition zones 39, 49 provide increased durability of the shaft 27 to bending fatigue and ease the insertion of the shaft 27 into the desired body cavity. The second flexible segment 41 may have a different diameter than the third segment 51, and the second flexible segment 41 may be disposed inside the third segment 51. In the preferred embodiment, the first and second flexible section 31, 41 have a diameter of approximately 7.2 French equal to approximately 2.16 millimeters, wherein the third segment 51 has a diameter of approximately 8.2 French equal to approximately 2.46 millimeters.

With reference to FIGS. 1, 9, and 10 the handle and viewing assembly 13 has a plurality of passageways, or channels, 88 in communication with corresponding passageways, or channels, 28 of shaft 27 and longitudinally extend to the first flexible shaft segment 31 to the input/output ports of the face tip assemblies 11-11'''. The passageways, or channels, between face tip assembly 11 and handle and viewing assembly 13 may be of equal diameter, or of differing diameter sizes, whereby they taper from one end to another to provide a smooth continuation of the passageways or channels.

With reference to FIGS. 1, 9, and 10, the handle and viewing assembly 13 includes: a distal section 81 which connects, or interfaces, with shaft 27, a working channel interface section 82 including a working channel interface assembly 72 which provides access for various operating tools through the instrument 10; a luminous conductor interface assembly 73 which provides for connecting, or interfacing, a light source such as a lamp box, for example, with the luminous conductor 63; and a proximal section 83 including proximal section assembly 84, including optical channel interface assembly 74, and which provides either an interface, or an intermediate connection, to a conventional imaging apparatus (not shown). The handle and viewing assembly 13 may include, if desired, any one or more of the following connection components: a handhold or pistol-type grip; a telescopic viewing assembly; an eyepiece adjustment; an optical tap for transmission of the optical image to an imaging apparatus; an electronic image enhancer/transmitter; and/or valve(s) for irrigation/suction.

The instrument 10 includes a working channel 71 for providing a pathway into the internal cavity for a conventional working instrument. Referring now to FIGS. 1, 2, 9 and 10, in the preferred embodiment, the working channel 71 is formed via passageways 28, 88 and provides working tool access to the interior cavity, the channel 71 extending from the working channel interface assembly 72 through to the operating tool port 21. In an embodiment, the working channel 71 has a substantially smooth interior surface to provide smooth movement of a working tool through instrument 10. The working channel 71 may have a substantially circular cross-sectional configuration, and may be coaxially surrounded by shaft segments 31, 41, and 51 of shaft 27. The interior wall surface 75 of working channel 71 may be coated with, or formed of, a material having a reduced coefficient of friction to facilitate easy passage and use of working accessories, or tools, in the working channel 71.

The instrument 10 includes at least one luminous conductor 63 for providing illumination within the interior cavity. The luminous conductor 63 extends from the luminous conductor interface assembly 73 of handle and viewing assembly 13, through shaft 27, to distal end 32 of first flexible shaft segment 31 to face assembly 11-11'''. The luminous conductor 63 is in the form of a fiber optic light carrying bundle. The luminous conductor interface assembly 73 provides a connector, as understood by those skilled in the art, between the luminous conductor 63 (light guide) and a conventional light source (not shown). Light travels through the luminous conductor interface assembly 73 and through the handle and viewing assembly housing 87 and shaft 27 to the interior cavity in a manner depending upon the configuration of the face tip assembly 11-11'''. For example, in one of the embodiments described with regard to FIG. 2, the luminous conductor 63 is a single fiber-optic bundle and may be interspersed among the optical conductor 62 in working channel 71. However, in one of the embodiments of FIG. 3, 4, or 5, the implementation may be best had through a plurality of independent fiber-optic bundles or a single fiber-optic bundle divided prior to or upon reaching luminous channel port 23. Also, in an embodiment, the luminous conductor interface assembly 73 may include an adjustable light valve (not shown) for selectively adjusting the intensity of the light. In another embodiment, the handle and viewing assembly 13 may include a plurality of the luminous conductor interface assemblies 73.

Referring again to FIGS. 1 and 9, an embodiment of the present invention also comprises at least one optical conductor 62 optically interfaced with the optical collector 61 for transmitting the gathered interior cavity image to the handle and viewing assembly 13. In the preferred embodiment, the optical conductor 62 is in the form of a fiber-optic bundle 64. In this embodiment, the instrument 10 includes an optical conductor channel 92 which encloses and receives the optical conductor 62, 64. The optical conductor 62, 64 may be located within the instrument 10, such as by disposing it in the working channel 71, or it may be formed as a separate channel. A luminous conductor channel 93 may be provided to carry light to the face tip assembly 11-11''' and correspondingly the internal cavity and thus, the area of interest. A fused fiber optic image bundle 62 would extend through shaft 27 to the face tip assembly 11-11''' and correspondingly to the optical image collector 61. In an embodiment, the optical conductor 62 is supported within handle and viewing assembly housing 87 by means known by those skilled in the art. For example, the optical conductor 62 would be supported within the handle and viewing assembly housing 87. The handle and viewing assembly 13 of endoscope 10 may be equipped to interface with an imaging apparatus 91 (FIG. 11) having an imaging processor 93 in order to capture the image gathered by optical image collector 61 in order to process the image for transmission to a human interface apparatus 101, such as a monitor and/or to video capable glasses. In an alternative embodiment, the handle and viewing assembly 13 is used as a form of telescope as known by those skilled in the art, whereby an ocular lens and lens support would cooperate with a spring means to permit relative movement between the optical conductor 62 and the housing 87 to provide direct, adjustable, visual imaging. In an embodiment, an optical wedge (not shown) is included, the optical wedge can be located near the distal end 32 of the first flexible segment 31 to provide a direction of view compensation of about 5-10 degrees when viewed under water, as would be the case if implemented as a ureteroscope.

Figure 11:
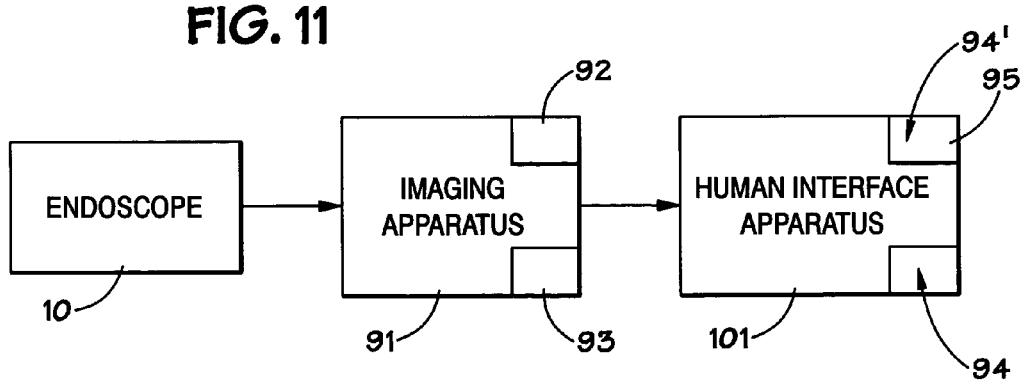
FIG. 11 is a schematic diagram of a system for viewing a visually obscured portion of a cavity.

Referring now to FIGS. 1, 2, and 11, a system to view a visually obscured portion of a body cavity will be described. The system may include an endoscope 10 as previously described. The system may further include an imaging apparatus 91 coupled with the at least one optical conductor 62 via the handle and viewing assembly 13, for capturing the image to send it to a human interface apparatus 101. In an embodiment, instead of the user strictly viewing the image gathered by the optical image collector 61 through a telescope or eye piece portion of a viewing assembly as is the case with much of the state-of-the-art, the handle and viewing assembly 13 of the present invention may include a proximal section assembly 84 which provides an interface for the imaging apparatus 91 as known by those skilled in the art. In an embodiment, the imaging apparatus 91 is an image transceiver 92 including an image processor 93 capable of providing video output to a human interface apparatus 101. In another embodiment, the imaging apparatus 91 is a pair of cameras optically coupled with a plurality of optical conductors 62. The preferred function of the imaging apparatus 91 is to render a three-dimensional image of the area of interest as selected by the user. Typically this is accomplished using individual "optical feeds." Additionally, in the preferred embodiment utilizing a pair of optical conductors 62 and optical image collectors 61, the imaging apparatus 91 captures each half of the image to render a complete and broader view of the area of interest.

The system may include a human-interface apparatus 101, as shown in FIG. 11. The human interface apparatus 101 is electrically or optically coupled with the imaging apparatus 91. In various embodiments, the human interface apparatus 101 may include such display/interface devices including a first image display device 94 such as a CRT, HDTV, for example, and in the preferred embodiment, a second image display device 94 including a video stereoscopic viewer unit 95 as known and understood by those skilled in the art. Although visual clarity is an important feature of the human interface apparatus 101, the invention is not limited to, or to the quality of, the examples provided above.

An embodiment of the present invention includes a method of performing a procedure in a visually obscured portion of a body cavity while under direct visual control. Specifically, the method of the present invention comprises the steps of: providing an endoscopic type instrument 10, having a face tip assembly, such as face tip assembly 11-11''' connected to a shaft assembly 12 having an actively flexible shat segment 31 at its distal end, the shaft assembly 12 being connected to a handle and viewing assembly 13; providing an illumination source, such as luminous conductor 62; inserting the distal end of the shaft assembly into a body cavity; manipulating the actively flexible shaft segment to a desired angular deflection in order to properly target, or view, the area of interest to allow both diagnosis and operative procedures. Another step may be advancing a working tool through the working channel 71, into the body cavity, while simultaneously monitoring its exit through the face tip assembly 11-11'''. The user can view the inner portion of a cavity such as, for example, the ureter or kidneys, and simultaneously view the insertion of a working/operating tool. Thus, various procedures can be carried out within the cavity while under direct visual control. The method may include the steps of irrigating the area of interest and suctioning particulate matter from the body cavity. Note, that one skilled in the art would know that some of the above steps do not need to be accomplished in the order provided in this embodiment. The method may also include the step of viewing during insertion, the relative location of the face tip assembly to properly position the assembly with respect to an area of interest 114;

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification. It is understood that other materials and dimensions may be used for the endoscopic type instrument of the present invention keeping in mind the dimensions of the affected body parts. Further, the number and dimensions of the channels or passageways employed are variable depending on the accessories (i.e. dye laser, fiber optics, etc.) used in conjunction with the instrument. Additionally, the actively flexible shaft segment could be used with other shaft segments which are all rigid, all semi-rigid, all flexible, or combinations thereof. Further, the face tip assemblies may be used with any type of endoscopic instrument or shaft assembly. Also, other shaped handles and handles of other designs may be used. Accordingly, the invention is to be limited only by the scope of the appended claims.

What is claimed is:

1. A ureteroscope system for viewing a visually obscured portion of a body cavity in a urinary system of a body comprising: a ureteroscope having, a face tip assembly, having at least one input/output port associated with a shaft assembly, the shaft assembly being associated with a handle and viewing assembly; the shaft assembly including a shaft having a distal end and at least three shaft segments for use in the body, the at least three shaft segments including an actively flexible shaft segment, having a length approximately between 2 cm. and 10 cm., disposed at the distal end of the shaft for insertion into the body cavity in the urinary system, a passively flexible shaft segment, having a length approximately between 5 cm. and 35 cm.; having a proximal end and a distal end, disposed adjacent the actively flexible shaft segment, and having the ability to readily flex within the body cavity in the urinary system without excessive deformation of the body cavity in the urinary system, a rigid shaft segment, having a length approximately between 25 cm. and 75 cm., disposed adjacent the handle and viewing assembly, the rigid shaft segment having a distal end, and the distal end of the rigid shaft segment being connected to the proximal end of the passively flexible shaft segment; at least one optical image collector adapted to gather an image from within the body cavity in the urinary system; at least one optical conductor, associated with the at least one optical image collector, and adapted to transmit the image to the handle and viewing assembly; at least one luminous conductor adapted to provide illumination to the body cavity in the urinary system; at least one working channel disposed within the shaft assembly adapted to permit a working instrument entry into the body cavity in the urinary system; and an imaging apparatus, associated with the at least one optical conductor, and adapted to capture the image to send it to a human interface apparatus adapted to permit viewing of the image.

2. The ureteroscope system of claim 1, including a working channel extension, associated with the face tip assembly, which includes at least one protrusion adapted to guide the working instrument and to prevent impact of foreign matter upon the at least one optical image collector.

3. The ureteroscope system of claim 1 wherein there are two optical conductors for producing a three-dimensional image.

4. The ureteroscope system of claim 3, including an image processor capable of capturing the image to render it three-dimensional for display by the human interface apparatus.

5. The ureteroscope system of claim 1 wherein there are two image collectors for producing a three-dimensional image.

6. The ureteroscope system of claim 1, including a semi-rigid shaft segment.

7. The ureteroscope system of claim 6, wherein the semi-rigid shaft segment is disposed adjacent the rigid shaft segment.

8. A ureteroscope for viewing a portion of a body cavity in a urinary system in a body, comprising: a face tip assembly, having at least one input/output port, associated with a shaft assembly, the shaft assembly being associated with a handle and viewing assembly; the shaft assembly including a longitudinal axis, a shaft having a distal end, and at least three shaft segments for use in the body, the at least three shaft segments including an actively flexible shaft segment, having a length approximately between 2 cm. and 10 cm., disposed at the distal end of the shaft for insertion into the body cavity in the urinary system, a passively flexible shaft segment, having a length approximately between 5 cm. and 35 cm.; having a proximal end and a distal end, disposed adjacent the actively flexible shaft segment and having the ability to readily flex within the body cavity in the urinary system without excessive deformation of the body cavity in the urinary system, a rigid shaft segment, having a length approximately between 25 cm. and 75 cm., disposed adjacent the handle and viewing assembly, the rigid shaft segment having a distal end, and the distal end of the rigid shaft segment being connected to the proximal end of the passively flexible shaft segment; at least one optical image collector adapted to gather an image from within the body cavity in the urinary system; at least one optical conductor, associated with the at least one optical image collector, and adapted to transmit the image to the handle and viewing assembly; at least one luminous conductor adapted to provide illumination to the body cavity in the urinary system; and at least one working channel disposed within the shaft assembly and adapted to permit a working instrument entry into the body cavity in the urinary system.

9. The ureteroscope of claim 8, including a working channel extension, associated with the face tip assembly which includes at least one protrusion to guide the working instrument and to prevent impact of foreign matter upon the at least one optical image collector.

10. The ureteroscope of claim 9, wherein the at least one optical image collector lies in a first plane which is disposed substantially perpendicular to the longitudinal axis of the shaft assembly; and the at least one protrusion is disposed at the distal end of the shaft forward of the first plane in which the at least one optical image collector lies, whereby the at least one optical image collector may view an operating tool passing forwardly beyond the at least one protrusion.

11. The ureteroscope of claim 10, wherein the plurality of input/output ports include at least one operating tool port, and the operating tool port lies in a second plane which is disposed substantially parallel with the first plane in which the at least one optical collector lies.

12. The ureteroscope of claim 11, wherein the first plane and the second plane are substantially coplanar.

13. The ureteroscope of claim 11, wherein the second plane is disposed in a spaced relationship from the first plane, toward the distal end of the shaft.

14. The ureteroscope of claim 9, wherein the at least one protrusion has two peaks which extend forwardly toward a distal end of the face tip assembly.

15. The ureteroscope of claim 14, wherein the plurality of input/output ports include at least one operating tool port, having two sides, and the two peaks are spaced apart from each other, with a peak disposed adjacent each side of the operating tool port.

16. The ureteroscope of claim 15, wherein the peaks are disposed offset from the longitudinal axis, with a substantial portion of each peak disposed below the longitudinal axis.

17. The ureteroscope of claim 8, wherein the plurality of input/output ports include at least one operating tool port, at least one optical image channel port, and at least one luminous channel port.

18. The ureteroscope of claim 8, wherein the face tip assembly includes at least two optical image collectors, each optical image collector being disposed in a first plane which is disposed substantially perpendicular to the longitudinal axis of the shaft assembly.

19. The ureteroscope of claim 8, including a semi-rigid shaft segment.

20. The ureteroscope of claim 19, wherein the semi-rigid shaft segment is disposed adjacent the rigid shaft segment.

21. A ureteroscope for viewing a portion of a body cavity in a urinary system in a body, comprising: a face tip assembly, having at least one input/output port, associated with a shaft assembly, the shaft assembly being associated with a handle and viewing assembly; the shaft assembly including a longitudinal axis, a shaft having a distal end, and at least three shaft segments for use in the body, the at least three shaft segments including an actively flexible shaft segment, having a length approximately between 2 cm. and 10 cm., disposed at the distal end of the shaft for insertion into the body cavity in the urinary system, a passively flexible shaft segment, having a length approximately between 5 cm. and 35 cm.; having a proximal end and a distal end, disposed adjacent the actively flexible shaft segment, and having the ability to readily flex within the body cavity in the urinary system without excessive deformation of the body cavity in the urinary system, a rigid shaft segment, having a length approximately between 25 cm. and 75 cm., disposed adjacent the handle and viewing assembly, the rigid shaft segment having a distal end, and the distal end of the rigid shaft segment being connected to the proximal end of the passively flexible shaft segment; at least two optical image collectors which produce a three dimensional image from within the body cavity in the urinary system; at least one optical conductor, associated with the at least two optical image collectors, and adapted to transmit the three dimensional image to the handle and viewing assembly; at least one luminous conductor adapted to provide illumination to the body cavity in the urinary system; and at least one working channel disposed within the shaft assembly and adapted to permit a working instrument entry into the body cavity in the urinary system.

22. The ureteroscope of claim 21, including a working channel extension, associated with the face tip assembly which includes at least one protrusion to guide the working instrument and to prevent impact of foreign matter upon the at least one optical image collector.

23. The ureteroscope of claim 22, wherein the at least two optical image collectors lie in a first plane which is disposed substantially perpendicular to the longitudinal axis of the shaft assembly; and the at least one protrusion is disposed at the distal end of the shaft forward of the first plane in which the at least two optical image collectors lie, whereby the at least two optical image collectors may view an operating tool passing forwardly beyond the at least one protrusion.

24. The ureteroscope of claim 23, wherein the plurality of input/output ports include at least one operating tool port, and the operating tool port lies in a second plane which is disposed substantially parallel with the first plane in which the at least one optical collector lies.

25. The ureteroscope of claim 24, wherein the first plane and the second plane are substantially coplanar.

26. The ureteroscope of claim 24, wherein the second plane is disposed in a spaced relationship from the first plane, toward the distal end of the shaft.

27. The ureteroscope of claim 23, wherein the at least one protrusion has two peaks which extend forwardly toward a distal end of the face tip assembly.

28. The ureteroscope of claim 27, wherein the plurality of input/output ports include at least one operating tool port, having two sides, and the two peaks are spaced apart from each other, with a peak disposed adjacent each side of the operating tool port.

29. The ureteroscope of claim 28, wherein the peaks are disposed offset from the longitudinal axis, with a substantial portion of each peak disposed below the longitudinal axis.

30. The ureteroscope of claim 21, including a semi-rigid shaft segment.

31. The ureteroscope of claim 30, wherein the semi-rigid shaft segment is disposed adjacent the rigid shaft segment.

32. A cystoscope system for viewing a visually obscured portion of a body cavity in a urinary system of a body comprising: a cystoscope having, a face tip assembly, having at least one input/output port associated with a shaft assembly, the shaft assembly being associated with a handle and viewing assembly; the shaft assembly including a shaft having a distal end and at least three shaft segments for use in the body, the at least three shaft segments including an actively flexible shaft segment, having a length approximately between 2 cm. and 10 cm., disposed at the distal end of the shaft for insertion into the body cavity in the urinary system, a passively flexible shaft segment, having a length approximately between 3 cm. and 14 cm.; having a proximal end and a distal end, disposed adjacent the actively flexible shaft segment, and having the ability to readily flex within the body cavity in the urinary system without excessive deformation of the body cavity in the urinary system, a rigid shaft segment, having a length approximately between 8 cm. and 40 cm., disposed adjacent the handle and viewing assembly, the rigid shaft segment having a distal end, and the distal end of the rigid shaft segment being connected to the proximal end of the passively flexible shaft segment; at least one optical image collector adapted to gather an image from within the body cavity in the urinary system; at least one optical conductor, associated with the at least one optical image collector, and adapted to transmit the image to the handle and viewing assembly; at least one luminous conductor adapted to provide illumination to the body cavity in the urinary system; at least one working channel disposed within the shaft assembly adapted to permit a working instrument entry into the body cavity in the urinary system; and an imaging apparatus, associated with the at least one optical conductor, and adapted to capture the image to send it to a human interface apparatus adapted to permit viewing of the image.

33. The cystoscope system of claim 32, including a working channel extension, associated with the face tip assembly, which includes at least one protrusion adapted to guide the working instrument and to prevent impact of foreign matter upon the at least one optical image collector.

34. The cystoscope system of claim 32 wherein there are two optical conductors for producing a three-dimensional image.

35. The cystoscope system of claim 34, including an image processor capable of capturing the image to render it three-dimensional for display by the human interface apparatus.

36. The cystoscope system of claim 32 wherein there are two image collectors for producing a three-dimensional image.

37. The cystoscope system of claim 32, including a semi-rigid shaft segment.

38. The cystoscope system of claim 37, wherein the semi-rigid shaft segment is disposed adjacent the rigid shaft segment.

39. A cystoscope for viewing a portion of a body cavity in a urinary system in a body, comprising: a face tip assembly, having at least one input/output port, associated with a shaft assembly, the shaft assembly being associated with a handle and viewing assembly; the shaft assembly including a longitudinal axis, a shaft having a distal end, and at least three shaft segments for use in the body, the at least three shaft segments including an actively flexible shaft segment, having a length approximately between 2 cm. and 10 cm., disposed at the distal end of the shaft for insertion into the body cavity in the urinary system, a passively flexible shaft segment, having a length approximately between 3 cm. and 14 cm.; having a proximal end and a distal end, disposed adjacent the actively flexible shaft segment, and having the ability to readily flex within the body cavity in the urinary system without excessive deformation of the body cavity in the urinary system, a rigid shaft segment, having a length approximately between 8 cm. and 40 cm., disposed adjacent the handle and viewing assembly, the rigid shaft segment having a distal end, and the distal end of the rigid shaft segment being connected to the proximal end of the passively flexible shaft segment; at least one optical image collector adapted to gather an image from within the body cavity in the urinary system; at least one optical conductor, associated with the at least one optical image collector, and adapted to transmit the image to the handle and viewing assembly; at least one luminous conductor adapted to provide illumination to the body cavity in the urinary system; and at least one working channel disposed within the shaft assembly and adapted to permit a working instrument entry into the body cavity in the urinary system.

40. The cystoscope system of claim 39, including a working channel extension, associated with the face tip assembly which includes at least one protrusion to guide the working instrument and to prevent impact of foreign matter upon the at least one optical image collector.

41. The cystoscope system of claim 40, wherein the at least one optical image collector lies in a first plane which is disposed substantially perpendicular to the longitudinal axis of the shaft assembly; and the at least one protrusion is disposed at the distal end of the shaft forward of the first plane in which the at least one optical image collector lies, whereby the at least one optical image collector may view an operating tool passing forwardly beyond the at least one protrusion.

42. The cystoscope system of claim 41, wherein the plurality of input/output ports include at least one operating tool port, and the operating tool port lies in a second plane which is disposed substantially parallel with the first plane in which the at least one optical collector lies.

43. The cystoscope system of claim 42, wherein the first plane and the second plane are substantially coplanar.

44. The cystoscope system of claim 42, wherein the second plane is disposed in a spaced relationship from the first plane, toward the distal end of the shaft.

45. The cystoscope system of claim 40, wherein the at least one protrusion has two peaks which extend forwardly toward a distal end of the face tip assembly.

46. The cystoscope system of claim 45, wherein the plurality of input/output ports include at least one operating tool port, having two sides, and the two peaks are spaced apart from each other, with a peak disposed adjacent each side of the operating tool port.

47. The cystoscope system of claim 46, wherein the peaks are disposed offset from the longitudinal axis, with a substantial portion of each peak disposed below the longitudinal axis.

48. The cystoscope system of claim 39, wherein the plurality of input/output ports include at least one operating tool port, at least one optical image channel port, and at least one luminous channel port.

49. The cystoscope system of claim 39, wherein the face tip assembly includes at least two optical image collectors, each optical image collector being disposed in a first plane which is disposed substantially perpendicular to the longitudinal axis of the shaft assembly.

50. The cystoscope system of claim 39, including a semi-rigid shaft segment.

51. The cystoscope system of claim 50, wherein the semi-rigid shaft segment is disposed adjacent the rigid shaft segment.

52. A cystoscope for viewing a portion of a body cavity in a urinary system in a body, comprising: a face tip assembly, having at least one input/output port, associated with a shaft assembly, the shaft assembly being associated with a handle and viewing assembly; the shaft assembly including a longitudinal axis, a shaft having a distal end, and at least three shaft segments for use in the body, the at least three shaft segments including an actively flexible shaft segment disposed, having a length approximately between 2 cm. and 10 cm., at the distal end of the shaft for insertion into the body cavity in the urinary system, a passively flexible shaft segment, having a length approximately between 3 cm. and 14 cm.; having a proximal end and a distal end, disposed adjacent the actively flexible shaft segment, and having the ability to readily flex within the body cavity in the urinary system without excessive deformation of the body cavity in the urinary system, a rigid shaft segment disposed adjacent the handle and viewing assembly, the rigid shaft segment, having a length approximately between 8 cm. and 40 cm., having a distal end, and the distal end of the rigid shaft segment being connected to the proximal end of the passively flexible shaft segment; at least two optical image collectors which produce a three dimensional image from within the body cavity in the urinary system; at least one optical conductor, associated with the at least two optical image collectors, and adapted to transmit the three dimensional image to the handle and viewing assembly; at least one luminous conductor adapted to provide illumination to the body cavity in the urinary system; and mat least one working channel disposed within the shaft assembly and adapted to permit a working instrument entry into the body cavity in the urinary system.

53. The cystoscope system of claim 52, including a working channel extension, associated with the face tip assembly which includes at least one protrusion to guide the working instrument and to prevent impact of foreign matter upon the at least one optical image collector.

54. The cystoscope system of claim 53, wherein the at least two optical image collectors lie in a first plane which is disposed substantially perpendicular to the longitudinal axis of the shaft assembly; and the at least one protrusion is disposed at the distal end of the shaft forward of the first plane in which the at least two optical image collectors lie, whereby the at least two optical image collectors may view an operating tool passing forwardly beyond the at least one protrusion.

55. The cystoscope system of claim 54, wherein the plurality of input/output ports include at least one operating tool port, and the operating tool port lies in a second plane which is disposed substantially parallel with the first plane in which the at least one optical collector lies.

56. The cystoscope system of claim 55, wherein the first plane and the second plane are substantially coplanar.

57. The cystoscope system of claim 55, wherein the second plane is disposed in a spaced relationship from the first plane, toward the distal end of the shaft.

58. The cystoscope system of claim 54, wherein the at least one protrusion has two peaks which extend forwardly toward a distal end of the face tip assembly.

59. The cystoscope system of claim 58, wherein the plurality of input/output ports include at least one operating tool port, having two sides, and the two peaks are spaced apart from each other, with a peak disposed adjacent each side of the operating tool port.

60. The cystoscope system of claim 59, wherein the peaks are disposed offset from the longitudinal axis, with a substantial portion of each peak disposed below the longitudinal axis.

61. The cystoscope system of claim 52, including a semi-rigid shaft segment.

62. The cystoscope system of claim 61, wherein the semi-rigid shaft segment is disposed adjacent the rigid shaft segment.

* * * * *

UNITED STATES PATENT AND TRADEMARK OFFICE
CERTIFICATE OF CORRECTION

| | | |
|---|---|---|
| PATENT NO. | : 8,075,478 B2 | Page 1 of 1 |
| APPLICATION NO. | : 10/829833 | |
| DATED | : December 13, 2011 | |
| INVENTOR(S) | : Jorge A. Campos | |

It is certified that error appears in the above-identified patent and that said Letters Patent is hereby corrected as shown below:

In Col. 2, line 20, delete "property", and insert --properly--.

In Col. 3, line 19, after "pressure", insert --,--.
In Col. 3, line 26, delete "instrument", and insert --instrument's--.

In Col. 6, lines 50-51, delete "ureterscope", and insert --ureteroscope--.

In Col. 9, line 44, delete "11", and insert --11'--.

In Col. 11, line 3, delete "11", and insert --11"--.
In Col. 11, line 8, delete "63", and insert --62--.
In Col. 11, line 9, delete "11'", and insert --11"--.
In Col. 11, line 19, delete "111''", and insert --11'''--.
In Col. 11, line 24, delete "111''", and insert --11'''--.
In Col. 11, line 39, delete "11", and insert --11'''--.
In Col. 11, line 22, delete "69", and insert --60--.

In Col. 12, line 4, delete "22-23" and insert --23-23"--.
In Col. 12, line 58, delete "shaft t", and insert --shaft--.

In Col. 13, line 39, delete "a".

Signed and Sealed this
Eighth Day of May, 2012

David J. Kappos
*Director of the United States Patent and Trademark Office*